United States Patent
Charollais et al.

(10) Patent No.: US 6,171,511 B1
(45) Date of Patent: Jan. 9, 2001

(54) THERMAL ETCHING PROCESS OF A CERAMIC UNDER OXIDIZING CONDITIONS

(75) Inventors: François Charollais, Allemagne; Mireille Bauer, Manosque; Michel Coster, Cairon; Pascal Piluso, Aix-en-Provence; Claude Fort, Lagnes, all of (FR)

(73) Assignees: Commissariat a l'Energie Atomique, Paris; Compagnie Generale des Matieres Nucleaires, Velizy-Villacoublay, both of (FR)

( * ) Notice: Under 35 U.S.C. 154(b), the term of this patent shall be extended for 0 days.

(21) Appl. No.: 09/176,604

(22) Filed: Oct. 21, 1998

(30) Foreign Application Priority Data

Oct. 21, 1997 (FR) .................................................. 97-13168

(51) Int. Cl.⁷ .................................................. C04B 41/91
(52) U.S. Cl. .............................. 216/55; 216/58; 216/59; 216/60; 216/61; 216/63; 216/64; 216/76; 216/88
(58) Field of Search ................................ 216/55, 58, 59, 216/60, 61, 63, 64, 76, 88

(56) References Cited

U.S. PATENT DOCUMENTS

| | | | |
|---|---|---|---|
| 3,859,403 | * | 1/1975 | Kahn ...................................... 264/56 |
| 4,548,903 | | 10/1985 | Weiss et al. .............................. 436/5 |
| 4,702,869 | * | 10/1987 | Higuchi et al. ......................... 264/65 |
| 4,834,926 | * | 5/1989 | Iwasaki et al. ......................... 264/65 |

FOREIGN PATENT DOCUMENTS

| | | | |
|---|---|---|---|
| 616 339 A1 | | 9/1994 | (EP) . |
| 51-80999 | * | 7/1976 | (JP) . |
| 6-204008 | * | 1/1993 | (JP) . |
| 6-102159 | * | 4/1994 | (JP) . |

OTHER PUBLICATIONS

G. C. Grappiolo: "Thermal etching as a mean to evidence grain–boundaries in high density U02", Energia Nucleare, vol. 11, #5 May 1964 Milan, It, p. 273 XP002070329.

Abrefah J et al: "High temperature oxidation of U02 in steam–hydrogen mixtures", Journal of Nuclear materials, Jan. 1994, vol. 208, No. 1–2, pp. 98–110, XP002070330.

Sari C et al: "Ceramography of Uranium–Plutonium Oxides–2" Prakt Metallogr, Mar. 1970, vol, No. 3, pp. 146–52, XP002070331.

R.L. Colombo et al: "Thermal etching figures in ceramic bodies" Journal of Nuclear Materials, vol. 42, 1972, Amsterdam, NL, pp. 345–347, XP002070332.

V. Tebaldi, Kernforschung and Technologie, Metallography and Thermal Analysis of Ceramic Nuclear Fuels—a handbook for laboratory assistants and test engineers, commission of the European Community, 1988, EUR 11716DE, cited on p. 1, lines 29 to 32 in Germany.

* cited by examiner

Primary Examiner—Randy Gulakowski
Assistant Examiner—Anita Alanko
(74) Attorney, Agent, or Firm—Pearne & Gordon LLP

(57) ABSTRACT

The invention relates to a process for thermal etching under oxidizing conditions of a ceramic, more particularly with the aim of revealing its grain boundaries and for the study of its granular microstructure. The invention applies to technical and nuclear ceramics and in particular $UO_2$ and to $(U, Pu)O_2$ mixtures. The thermal etching is performed in a furnace or kiln under a controlled atmosphere constituted by an oxidizing gas supplying a chemical oxygen potential of –75 to –125 kJ/mole and comprises the following successive stages:

rapid rise in the temperature of the furnace to a rate of 900 to 1500° C./h from the initial temperature to a temperature plateau, maintaining the temperature at said plateau at a value of 1250 to 1450° C. for between 30 and 15 minutes, lowering the temperature to the final temperature.

19 Claims, 10 Drawing Sheets

THERMAL ETCHING PROCESS OF A CERAMIC UNDER OXIDIZING CONDITIONS

DESCRIPTION

The invention relates to a process for the thermal etching of a ceramic under oxidizing conditions with the particular aim of revealing its grain boundaries and studying its granular microstructure.

The invention applies to technical and nuclear ceramics and in particular to $UO_2$ and $(U, Pu) O_2$ mixtures.

The structural study of a material generally involves a careful metallographic preparation of said material for the morphological analysis thereof.

In order to study the structure, it is necessary to render visible the different constituent elements thereof and consequently, precisely reveal the grain boundaries in order to permit the measurement of the size of the grains of the material. In the case of polyphase materials, the size of the grains must be measured on each phase independently.

The automation of the measuring processes concerning the size of the grains involving image analysis software, requires the obtaining of high quality images. This quality is linked with that of the revealing of the grain boundaries and therefore the etching process used. Among the latter, reference can be made in the case of ceramics to acid chemical etching processes.

Chemical etching processes are e.g. described in the work by V. Tebaldi "Kernforschung und Technologie", *Metallography and Thermal Analysis of Ceramic Nuclear Fuels*—a handbook for laboratory assistants and test engineers, commission of the European Community, 1988, EUR 11716 DE.

From the physicochemical standpoint, chemical acid etching of a polished surface of a monophase sample, as is the case with $UO_2$, can be summarized by the action of two concurrent mechanisms:

an etching of the surface of the grains at different speeds as a function of their crystal orientation, said facetting of the grains inducing reflectivity differences, which will make it possible to individualize them during their observation by optical microscopy, a specific local etching at the grain boundaries, due to the significant crystal defects and to the presence of impurities. This etching will create a groove at the location of the grain boundary and its shape will depend on the surface and intergranular tensions. It is therefore directly linked with the crystal orientation differences of two adjacent grains and will therefore be heterogeneous in the plane of the specimen.

In the case of polyphase ceramics, such as mixed uranium and plutonium fuel, the chemical potentials of the different phases are not the same. These chemical potential differences are significant and will finally lead to a preferential etching of one phase compared with the other.

Therefore the revealing of the microstructure of $(U, Pu) O_2$ fuels corresponds to this principle.

This specificity enables scientists to independently study the granular structure of areas having high and low plutonium contents using two specific chemical etching processes:

a first etching process for revealing the areas having a limited Pu enrichment (matrix), which is carried out using an acid solution ($H_2O$, $H_2O_2$, $H_2SO_4$) at ambient temperature for 2 hours 20 minutes, the sample is then repolished before undergoing a second acid etching ($H_2O$, $H_2SO_4$, $NH_4NF_2$) at 70° C. for 1 to 3 minutes, which makes it possible to reveal all the surface including the areas with high and low plutonium contents.

However, it is particularly difficult to control the latter etching process, the areas with only a limited plutonium enrichment being liable to undergo an excessive revealing or development.

The chemical etching of a ceramic, particularly a nuclear fuel ceramic, especially of the $(U, Pu) O_2$ type involves a certain number of disadvantages, including:

impossibility of uniformly revealing a ceramographic section for the reasons mentioned hereinbefore, difficulty of defining a reproducible revealing procedure, because it is necessary to start with in each case new solutions, different colouring of the grains, generated by multiple crystal orientations of the grains, not permitting the automation of the grain size measurements, generation of active effluents (in the case of "nuclear" ceramics) and corrosion of neighbouring equipment by the giving off of acid vapours in the glove box.

The above shows that the use of chemical etching for revealing grain boundaries of a ceramic and in particular a ceramic acting as a nuclear fuel ("nuclear" ceramic) is unsatisfactory because, due to the incomplete revealing of the grain boundaries, the images obtained on the ceramic or fuel which has been chemically etched are of mediocre quality and do not permit the automatic processing and analysis of the images.

Another method for revealing grain boundaries is thermal etching, which is currently used for studying the granular structure of technical ceramics, such as e.g. alumina, silicon carbide or cerium oxide.

Thermal etching is based on the fact that on heating a polycrystalline solid to a temperature T in the presence of a vapour or liquid phase in thermodynamic equilibrium with the solid, grooves appear at the emergence lines of the grain boundaries as a result of material transfer diffusion mechanisms (surface diffusion, volume diffusion and condensation evaporation). This phenomenon is illustrated in FIG. 1, which shows the groove of the thermally revealed grain boundary.

The thermal etching of ceramics in general is performed under an atmosphere identical to that used during the production thereof.

The thermal etching of $UO_2$ has been studied, but only under the following specific conditions, which are those of a reducing, thermal etching. The thermal etching experiments disclosed in the literature are generally performed on $UO_2$ pellets, which have been previously annealed for sufficiently long periods of time, e.g. two weeks at 1700° C., in comparison with the thermal etching periods. This annealing is indispensable for stabilizing the microstructure and thus overcoming a possible enlargement of the grains, which could lead to mechanisms other than that or those responsible for the thermal etching of the groove. Studies carried out on $UO_{2+x}$ of a superstoichiometric nature were carried out with a uranium oxide, whose oxygen/uranium ratio was determined and which did not evolve during the experiment.

Thus, most of the publications describe the thermal etching of $UO_{2x}$ fuels under a high temperature close to 1650 to 1700° C. and in a reducing or neutral atmosphere.

Thus, the article by G. C. Grappiolo "Thermal etching as a mean to evidence grain boundaries in high density $UO_2$", energia nucleare, vol. 11, No. 5, May 1964 describes the treatment of high density uranium oxide in a hydrogen atmosphere at 1650° C.

In the same way, the article by R. L. Colombo and I. Amato "Thermal etching figures in ceramic bodies", *Journal of Nuclear Maerials* 42, (1972) 345–347, North Holland Publishing Co., Amsterdam, describes the thermal etching of ceramics such as alumina and $UO_2$ in a reducing hydrogen atmosphere at a temperature close to 1700° C.

As far as is known to us, the thermal etching of mixed plutonium and uranium oxides, such as MOX, has not been described in the literature.

The inventors have found, by carrying out thermal etching operations under a reducing atmosphere on $UO_2$ samples, particularly at 1650° C., under dry $H_2$ for 15 minutes, that the revealing of grain boundaries obtained by thermal etching under a reducing atmosphere are of better quality than those obtained after chemical etching operations, although a certain number of defects and disadvantages remained, more particularly:

an optical image of a non-uniform nature of the grain boundaries, so that the automatically binarized grain boundary network has discontinuities requiring a significant manual correction during the image treatment stage, the revealing of crystal defects, such as scratches or ridges on the surface of the material or dislocations and which generate a background noise, which becomes all the more prejudicial if the sample is porous, because confusion can arise between the porosity, the background noise and the grain boundary network, the necessity of a furnace technology adapted to thermal shocks and a rapid temperature rise to close to 1700° C.

Such a furnace technology is difficult to implement and very onerous. The fact of operating at such high temperatures, which can exceed the sintering temperature, is liable to favour granular growth phenomena able to bias the grain size measurement.

The inventors have also revealed identical phenomena during thermal etching under reducing conditions of (U, Pu) $O_2$ fuel.

Thus, thermal etching tests carried out with a mixture of argon, 5% hydrogen and 2600 pm $H_2O$ at high temperatures close to 1600° C. and for 10 to 30 minutes led to a revealing of the surface of the (U, Pu) $O_2$ fuels identical to that obtained in the case of uranium oxide, with in particular heterogeneities in the thermal etching of the grain boundaries.

Moreover, in the specific case of (U, Pu) $O_2$ fuels, reducing thermal etching, unlike chemical etching, does not make it possible to distinctly reveal the areas having high plutonium contents.

An etching difference as a function of the local plutonium content of the grains is not obtained during the thermal etching of (U, Pu) $O_2$ fuels under reducing conditions, namely under humidified hydrogen.

However, the exhaustive characterization of the nuclear fuel (U, Pu) $O_2$ makes it necessary to measure the size of the grains separately on the areas with high and low plutonium contents, which involves said areas being individually identifiable. This condition is not fulfilled by thermal etching under a reducing atmosphere according to the prior art.

The object of the present invention is to provide an etching process intended more particularly to reveal the granular structure of ceramics and in particular so-called "nuclear" ceramics such as $UO_2$ and (U, Pu) $O_2$, which does not suffer from the disadvantages, limitations and deficiencies of the prior art processes and which solves the problems which arise in the prior art etching processes.

This object and other objects are achieved by a process for the thermal etching of a ceramic in which, according to the invention, said thermal etching is performed in a furnace under a controlled atmosphere, constituted by an oxidizing gas supplying a chemical oxygen potential of −75 kJ/mole to −125 kJ/mole and which comprises the following, successive stages:

rapid temperature rise of the furnace at a rate of 900° C./h to 1500° C./h from the initial temperature to a temperature plateau, maintaining the temperature of said plateau at a value of 1250° C. to 1450° C. for a period 15 minutes to 30 minutes, lowering the temperature to the final temperature.

The thermal etching of ceramics is known in the prior art, but it is in fact an etching under a reducing atmosphere and at a high temperature and not an etching under an oxidizing atmosphere and at a low temperature.

Thermal etching under the conditions according to claim 1 has never been described or suggested in the prior art for all the ceramic types, no matter whether they are technical or nuclear ceramics.

The oxidizing, thermal etching process according to the invention, where working takes place at a relatively low temperature, i.e. 1250 to 1450° C., does not suffer from any of the disadvantages of chemical etching processes.

Thus, no acid solution is used, so that there is no equipment corrosion. In the case of nuclear ceramics, no radioactive effluent is generated, so that there is no need to have supplementary treatment installations downstream of the etching process.

Compared with thermal etching processes under a reducing atmosphere, the temperatures used in the process according to the invention (1250 to 1450° C.) are much lower, which makes it possible to use a furnace based on a simpler technology and which is therefore much less onerous. Thus, it is possible to replace the molybdenum resistors by much less fragile lanthanum chromite resistors.

The use of relatively low etching temperatures, below the sintering temperature, also makes it possible to limit granular growth phenomena and other phenomena liable to bias the measurements performed on the etched ceramic.

However, the essential characteristic of the process according to the invention, unlike in the prior art chemical and thermal processes, makes it possible to bring about ceramographic revealing of a quality hitherto not achieved.

Satisfactory optical images are obtained of the grain boundaries of the entire surface of the specimen or sample, which can be segmented and treated automatically by image analysis.

The surface of the ceramic is etched, uniformly revealed in a homogeneous manner, in other words all the grain boundaries are etched and revealed, and the geometry of the grooves of the grain boundaries is symmetrical, homogeneous and regular, unlike in the prior art processes where numerous grooves of grain boundaries have a clear asymmetry.

Such results are obtained by in particular adopting the specific oxygen chemical potential range according to the invention of between −75 and −125 kJ/mole and preferably of −100 kJ/mole.

Finally, the duration of the thermal etching according to the invention, which is preferably 15 to 30 minutes, is greatly reduced, which leads to a significant time gain.

The apparatus in which the thermal etching according to the invention is performed is a furnace, but this term covers any equipment, enclosure, etc., in which the etching can be carried out under the conditions of the process according to the invention.

It can e.g. be any adequate, thermal etching furnace, which generally has a low thermal inertia and which allows high temperature rise and possibly fall rates.

Among the furnace types suitable for the process according to the invention, reference is e.g. made to a vertical tubular furnace or a thermo-balance furnace.

The furnace is under a controlled atmosphere, which generally means that the composition of the atmosphere in the internal volume of the furnace is perfectly controlled, e.g. by carrying out a continuous scavenging of the interior of the furnace by the oxidizing gas at a regulated, given flow rate.

Any ceramic can be treated by the process according to the invention, no matter whether it is a so-called "technical" ceramic or a so-called "nuclear" ceramic.

The treated ceramic is constituted preferably by one or more refractory oxides of metals, e.g. chosen from among aluminium oxides, cerium oxides, metal oxides of the family of actinides such as $PuO_2$, $UO_2$ and $ThO_2$ and the mixed oxides of said metals such as $(U, Pu) O_2$.

The ceramic can be a monophase ceramic, but can also be a polyphase, e.g. biphase ceramic. The process according to the invention is applied with particular advantage to polyphase ceramics, whereof it makes it possible to reveal the different areas, which has hitherto been impossible.

Advantageously, according to the invention, said ceramic is a nuclear fuel, preferably in the form of a pellet, prepared from $UO_2$ powder, or a nuclear fuel of the MOX type. MOX is a nuclear fuel (a nuclear ceramic) usually prepared by pelletizing and sintering a mixture of uranium oxide and plutonium oxide powders according to the so-called MIMAS (MIcronization of MASterblend) process.

This production process generates a microstructure individual to the MOX nuclear fuel, in which the parent or mother mixture areas (plutoniferous islands with a high $PuO_2$ content) remain present in the matrix (area having a low $PuO_2$ content and essentially constituted by $UO_2$) after sintering and are the source of a peculiar distribution of the plutonium and the size of the grains within the pellet.

The characterization of this complex structure, which was hitherto extremely difficult, is rendered possible by the process according to the invention.

The process according to the invention, performed on MOX, has the supplementary advantage of effecting a selective etching, which makes it possible to separately reveal the matrix and the plutoniferous islands or parent mixture areas. This etching difference, obtained in a surprising manner through the process according to the invention, has never been obtained by thermal etching processes under reducing conditions and is due to the specific, oxygen chemical potential used in the process according to the invention of −75 to −125 kJ/mole and preferably −100 kJ/mole.

Thus, less oxidizing etching conditions with an oxygen chemical potential outside the aforementioned range and e.g. from −150 to −200 kJ/mole do not make it possible to distinguish plutoniferous islands with a high plutonium content from the remainder of the matrix.

The oxidizing gas is preferably constituted by a vector gas and oxygen.

The vector gas is preferably chosen from among $CO_2$, argon, other inert gases such as nitrogen and mixtures thereof.

Advantageously, the vector gas is $CO_2$. It has been found that $CO_2$ makes it possible to obtain better quality ceramographic revealing, because said gas is decomposed in situ at the temperatures of the heat treatment, thus supplying additional oxygen compared with the quantity indicated hereinafter (i.e. the oxygen proportion, after decomposition, is 100 to 3000 vpm instead of 10 to 3000 vpm, as hereinafter).

The oxygen proportion in the oxidizing gas is preferably in general 10 to 3000 vpm, preferably 100 to 1000 vpm and e.g. 1000 vpm.

A preferred oxidizing gas is (at the outset) constituted by $CO_2$ and 10 vpm oxygen. Another oxidizing gas is constituted by argon and 1000 vpm of oxygen. Thus, one is in the oxygen potential range according to the invention.

It has been shown hereinbefore that the etching temperature, i.e. the temperature of the plateau is 1250 to 1450° C., preferably 1300 to 1400° C. and a temperature close to 1350° C. would appear to be an excellent compromise with respect to the revealing quality and the image obtained.

Particularly preferred etching conditions are e.g. 1350° C., for 30 minutes and under a $CO_2$+10 vpm $O_2$ atmosphere for $UO_2$ and MOX ceramics. The furnace temperature drop following the plateau generally takes place at the same speed as the rise, i.e. a rate of 900 to 1500° C./h to the final temperature.

The initial and final temperatures are generally ambient temperature.

The process is generally performed under atmospheric pressure (1 atm).

Generally and prior to the actual thermal etching, i.e. before the ceramic has been introduced into the furnace, it undergoes a polishing treatment, e.g. using abrasive papers, whereof the grain size is successively ever smaller, e.g. to 15 μm. Generally a final polishing takes place with the aid e.g. of a felt covered with a diamond paste, with 1 μm grains.

The invention also relates to a process for the study of the microstructure of a ceramic wherein:

the granular structure of said ceramic is revealed by the thermal etching process according to the invention, as described hereinbefore, the thus revealed structure is subject to one or more analysis and/or measurement and/or observation operations.

Preferably, said operation can be any analysis and/or measurement and/or observation operation known to the expert, but preferably incorporates an observation of the surface of the ceramic by optical or electronic means and the measurement of the grain size.

Advantageously, the grain size measurement is carried out by using an analysis software for the images associated with said optical means, such as an optical microscope.

Finally, the invention relates to a thermally etched, polished ceramic, in which the surface of said ceramic is uniformly etched and the geometry of the grooves of the revealed grain boundaries is symmetrical, homogeneous and regular.

Other features and advantages of the invention can be gathered from the following description given in an illustrative and non-limitative manner with reference to the attached drawings.

DETAILED DESCRIPTION OF EMBODIMENTS OF THE INVENTION

Figure 1:
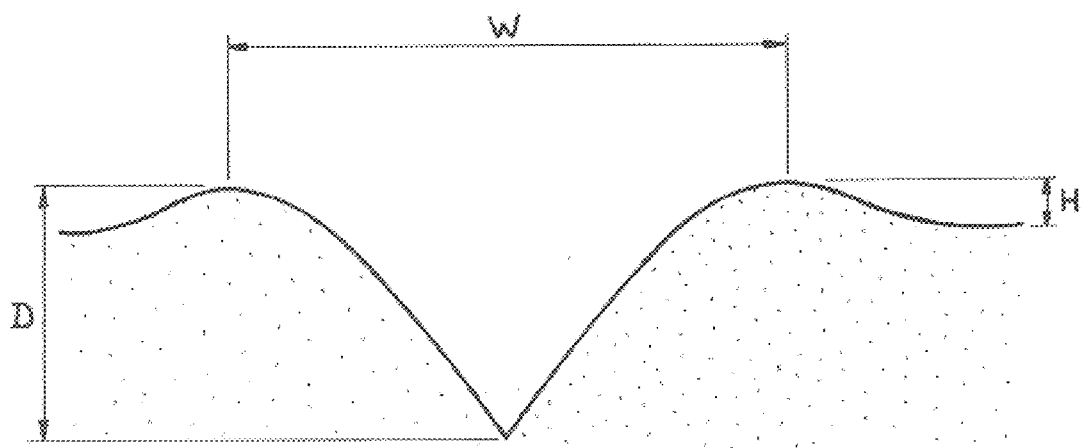
FIG. 1 is a lateral sectional view showing a groove at the grain boundary which has been thermally revealed.

The following description and examples illustrate the preparations of $UO_2$ and MOX nuclear ceramic samples, their treatment by a chemical etching process, by a thermal etching process under a reducing atmosphere, and by the thermal etching process under an oxidizing atmosphere according to the invention, as well as the results obtained by this treatment and the measurement of the size of the grains performed on treated ceramics, whereof the microstructure has been revealed by the etching operation.

1. Preparation of the samples 1.1. Characteristics of the studied samples ($UO_2$ and MOX).

The studied uranium oxide pellets came from 3 batches of samples produced (A, B, C), namely from uranium dioxide powders of different natures (dry route or wet route batch 1 and batch 2), or sintered under different conditions.

The MOX fuel pellets are obtained from two batches (MOX 1 and MOX 2) produced under similar conditions in accordance with the MIMAS (MIcronization of MASterblend) process with the two types of $UO_2$ powders wet route batch 1 and batch 2.

The $PuO_2$ powder used is from the La Hague reprocessing plant and is in the form of square based lamellar platelets or wafers.

The MIMAS process is known to the expert and will not be described here.

1.2. Ceramographic preparation of the samples.

The preparation of the samples, cutting up and polishing constitutes a vital stage for the microstructural study of the materials by image analysis. It must be carried out particularly carefully and in a manner adapted to the studied materials.

The samples, which are cylindrical pellets with a diameter of 8 mm and a height of 12 mm, all have relatively high densities of a similar nature and close to 95%. The ceramographic preparation of the samples is consequently carried out according to the same procedure.

Following cutting up and coating in a resin, such as an Araldite resin, a series of prepolishing operations are carried out on different abrasive papers of respective grain sizes 76, 35, 22 and 15 μm, followed by a final polishing using a felt covered with a diamond paste with grains of approximately 1 μm.

The surface is cleaned between each (pre)polishing stage by immersing the sample in an aqueous bath exposed to ultrasonics. Stripping takes place by a limited heating of the resin which, on expansion, permits the release of the sample.

2. Experimental thermal etching equipment

The special feature of a thermal etching furnace is mainly its low thermal inertia, permitting considerable temperature rise (and fall) rates. Two types of furnaces are used in the following examples as a function of the considered atmosphere and/or considered oxide ($UO_2$ or (U,Pu) $O_2$).

2.1. Vertical tubular furnace.

A PYROX VT 30$^{(R)}$ vertical tubular furnace is used for thermal etching, under oxidizing conditions, of $UO_2$, i.e. within the scope of the process according to the invention. This furnace is heated by four lanthanum chromite resistors.

The working tube placed in the centre of the four resistors is of dense, tight $Al_2O_3$.

The tight connection of a stainless steel flange to each end of the tube makes it possible to work under a controlled atmosphere. A water circulation ensures the cooling of the flanges.

In order to check both the sealing of the furnace and the oxygen content of the different gases used (Ar+10 vpm $O_2$, $CO_2$+10 vpm $O_2$), an oxygen gauge (zirconia probe) connected at the furnace outlet, measures the partial oxygen pressure of the atmosphere.

The maximum temperature rise and fall rates, essentially limited by the thermal shock resistance of the alumina tube, are 1200° C./h.

A precise positioning of the sample, both in the isothermal area of the furnace and at 1.5 cm from the measuring thermocouple, makes it possible to guarantee a precision of the temperature on the sample of ±50° C.

The gas supply is controlled as regards rate and pressure (flow rate 10 l/h). The furnace enclosure is under atmospheric pressure under normal use conditions.

2.2. Thermobalance furnace.

The study of the thermal etching of the MOX fuel and uranium oxide under reducing atmosphere (under $H_2$) or oxidizing atmosphere ($CO_2$) according to the prior art was performed in a NETZSCH STA 429$^{(R)}$ thermo-balance furnace placed in a glove box. The working tube is of dense, tight $Al_2O_3$. The experimental parameters are similar to those of the aforementioned equipment, namely:

temperature rise and fall rates of 1200° C./h, precision for the temperature measurement _+5° C., gas flow rate ($H_2$ or $CO_2$) 10 l/h.

The furnace enclosure is under atmospheric pressure.

The following examples 1 to 5 illustrate the thermal and chemical etching operations performed on $UO_2$ fuel.

EXAMPLE 1

In this example chemical etching takes place on samples of batches of $UO_2$ A, B and C. Chemical etching was carried out using an acid solution ($H_2O$, $H_2O_2$, $H_2SO_4$).

Figure 2:
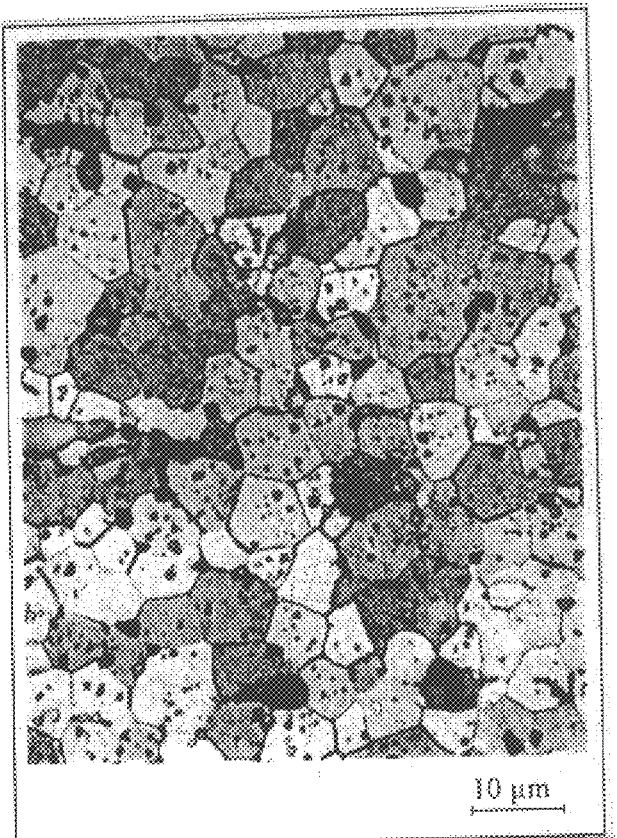
FIG. 2 is an optical image of a sample of batch A of $UO_2$, which has been chemically revealed.

The microstructure revealed by the chemical etching (cf. FIG. 2 relative to the chemical etching of a sample of batch A) illustrates the disadvantages of such etching, namely inter alia a different colouring of the sections of the grains and an incomplete revealing of the grain boundaries.

EXAMPLE 2

In this example, thermal etching takes place under a dry atmosphere (dry $H_2$) of samples of batches of $UO_2$, A, B and C.

The operating conditions for these experiments, performed under a dry hydrogen atmosphere, are summarized in the following I, the temperature rise and fall rates being fixed at 1200° C./h.

TABLE I

Operating conditions for the experiments performed under dry $H_2$

| Temperature (° C.) | Etching period (min) |
|---|---|
| 1550 | 30 |
| 1550 | 60 |
| 1600 | 15 |
| 1600 | 30 |
| 1650 | 15 |
| 1650 | 30 |

Optical observation of the etched microstructures (cf. FIG. 3) shows that the best result is obtained for the following temperature and duration parameters: 1650° C. and 15 min.

Figure 3:
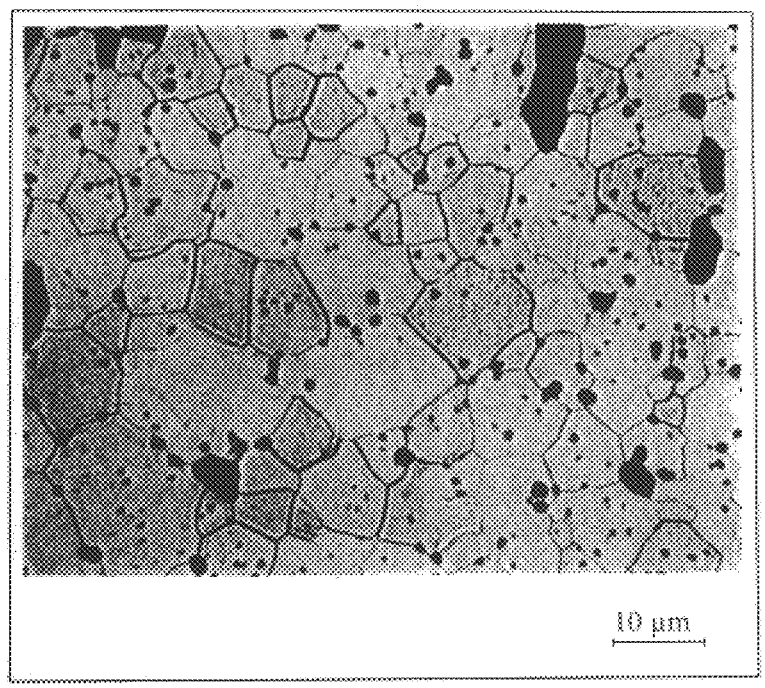
FIG. 3 is an optical image of a sample of batch A of $UO_2$ after thermal etching for 15 minutes at 1650° C. and under dry $H_2$.

Although the revealing is of a better quality than obtained after chemical etching, a certain number of the aforementioned disadvantages still remain, namely a non-uniform, resulting optical image (cf. FIG. 3).

Thus, the automatically binerized, grain boundary network has discontinuities requiring a significant manual correction during the image processing stage (cf. FIG. 3). Crystal defects such as ridges appear on the surface of the material or as dislocations. These defects generate a background noise, which becomes all the more disturbing when the sample is porous, because confusion can occur between the porosity, the background noise and the grain boundary network. It is necessary to have a furnace technology adapted to the thermal shock and to a rapid temperature rise close to 1700° C.

EXAMPLE 3

In this example, according to the invention, thermal etching takes place under an oxidizing atmosphere of a sample of $UO_2$ batch A. The oxidizing atmosphere is constituted by argon and 10 vpm $O_2$.

The operating conditions of the different tests are summarized in the following table II.

TABLE II

Operating conditions for thermal etching under Ar + 10 vpm $O_2$

| Temperature (° C.) | Etching period (min) |
|---|---|
| 1300 | 60 |
| 1550 | 30 |
| 1600 | 30 |
| 1650 | 10 |
| 1650 | 30 |
| 1680 | 5 |

The ceramographic revealing effects are comparable to those obtained by thermal etching under dry $H_2$ and suffer from the same disadvantages (heterogeneous revealing of the grain boundaries, revealing of crystal defects, etc.). The best results are obtained with the following thermal etching parameters (temperature, plateau duration): 1650° C., 15 min and 1680° C., 5 min.

The oxygen chemical potential of this gaseous mixture varies from −150 to −200 kJ/mole between 1300 and 1700° C. and is consequently outside the range of values defined in the process according to the invention, which also operates at lower temperatures.

EXAMPLE 4

In this example, according to the invention, thermal etching takes place under an oxidizing atmosphere of samples from $UO_2$ batches A, B and C. The oxidizing atmosphere is constituted by $CO_2$ and 10 vpm of $O_2$. The operating conditions of the different tests are summarized in table III.

The only invariant parameter is the duration of the thermal etching, fixed at 30 minutes.

TABLE III

Operating conditions for thermal etching under $CO_2$ + 10 vpm $O_2$

|  | Etching temperature (° C.) | Furnace pressure (atm) |
|---|---|---|
| Batch A | 1250 | 1 atm |
|  | 1350 |  |
|  | 1450 |  |
| Batch B | 1250 | 1 atm |
|  | 1350 |  |
|  | 1450 |  |
| Batch C | 1250 | 1 atm |
|  | 1350 |  |
|  | 1450 |  |

The oxidizing thermal etching performed under an atmosphere of $CO_2$ and $O_2$ 10 vpm gives excellent quality ceramographic revealing effects and a very homogeneous thermal etching at the grain boundaries. There is in particular an absence of etching figures present following thermal etching under a reducing atmosphere, e.g. of $H_2$.

EXAMPLE 5

In this example the size of the grains is measured and the interest of thermal etching under oxidizing atmosphere of $CO_2$ is demonstrated for revealing the microstructure of $UO_2$-based nuclear fuels. It is in particular shown that no modification, in terms of granular growth, is produced by this etching procedure.

In order to do this, the grain size densities with respect to the equivalent diameter to the sections of the grains are compared between chemical etching under the aforementioned conditions and thermal etching according to the invention in an oxidizing atmosphere under $CO_2+10$ vpm $O_2$ (cf. example 4).

Determination also takes place of the mean diameter established by rangewise analysis and the quartiles are also calculated. They make it possible to characterize the dispersion of the grain size distributions of the different etching operations.

Application has taken place of a sampling plan involving the analysis of a minimum of 1800 sections of grains according to a stratified random layout of the measuring ranges.

This example studies the influence of the etching temperature, namely 1250, 1350 and 1450° C. on uranium dioxide samples of batches A, B and C. In all cases, the etching time is 30 minutes.

Figure 4:
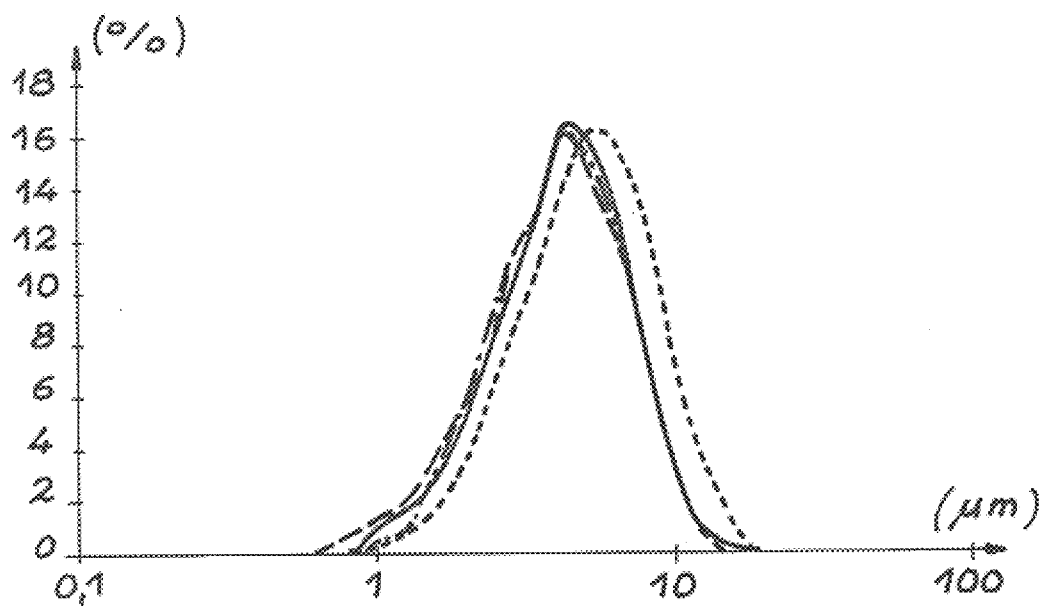
FIG. 4 is a graph giving the grain size density curves of a sample of batch A of $UO_2$ obtained following a chemical etching (mixed line curve) and thermal etching operations under an atmosphere of $CO_2$+10 vpm $O_2$ at 1250° C., 1350° C. and 1450° C. (respectively large dot, continuous line and small dot curves), the frequency in % being plotted on the ordinate and the equivalent diameter in μm on the abscissa.
Figure 5:
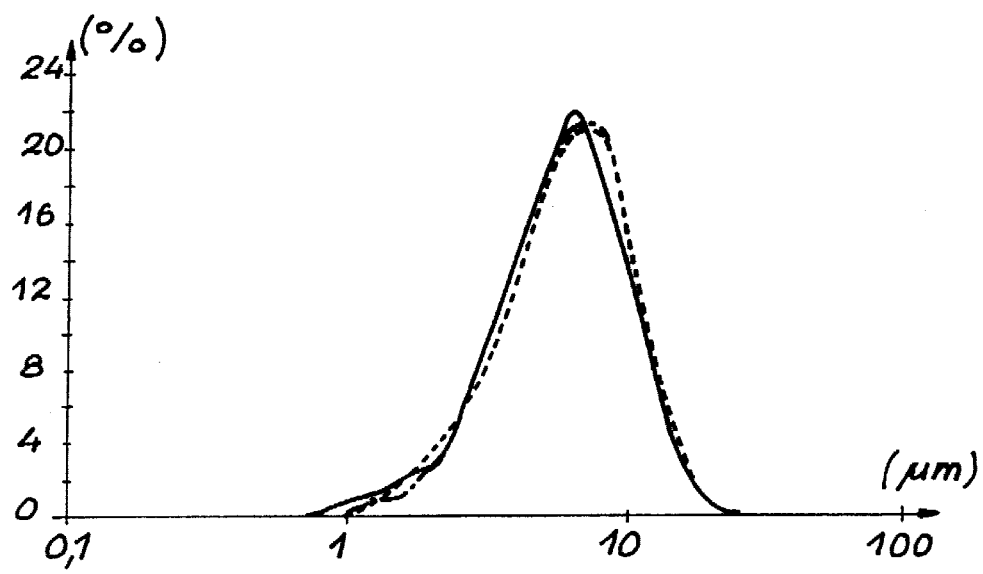
FIG. 5 is a graph identical to FIG. 4 giving the grain size density curves of batch B of $UO_2$ obtained following chemical etching (mixed line curve) and thermal etching operations under an atmosphere of $CO_2$+10 vpm of $O_2$ at 1350° C. and 1450° C. (respectively continuous line and small dot curves).
Figure 6:
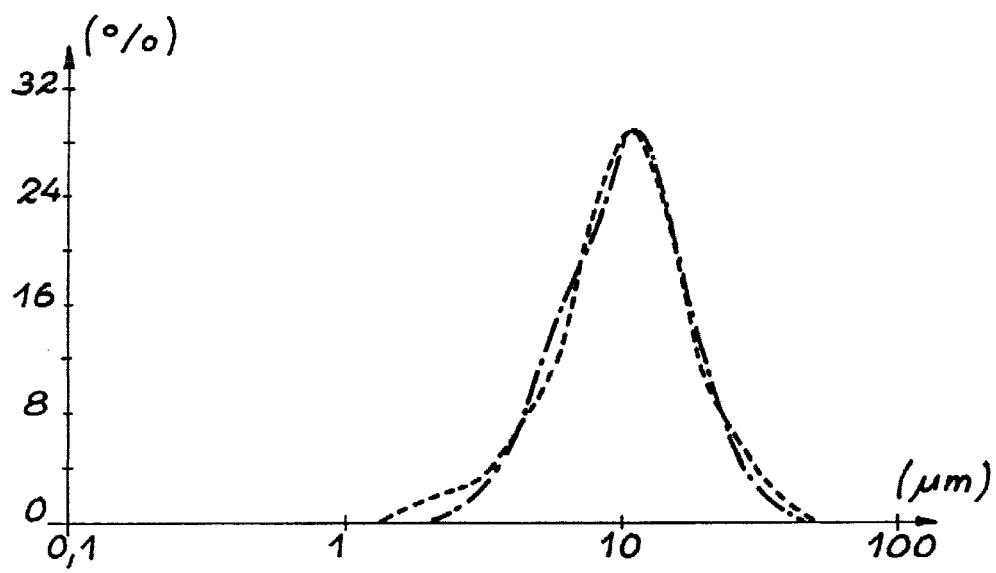
FIG. 6 is a graph identical to FIGS. 4 and 5 giving the grain size density curves of batch C of $UO_2$ after chemical etching and thermal etching under an atmosphere of $CO_2$+10 vpm of $O_2$ at 1450° C.

The grain size densities obtained are shown in FIGS. 4, 5 and 6 for samples of batches A, B and C. The surface state of the three samples after the etching operations is also observed. The conclusions which can be drawn from this study are indicated below for each of the treated batches.

Batch A : It would appear that the material can be etched up to a temperature of 1350° C., without any significant evolution of the microstructure.

It can be seen that the three grain size density curves, respectively for thermal etching at 1250 and 1350° C. and for chemical etching are superimposed and that the mean size does not evolve between the different etching operations and remains close to 5 $\mu$m. For said batch, a temperature of 1250° C. would appear to represent a lower temperature limit for ceramographic revealing. However, the eye is still able to see the grain boundary network.

At 1450° C. there is a certain granular growth, at least on the surface, so that revealing is slightly inferior at this temperature.

An examination of the surface of a sample etched at this temperature makes it possible to observe a slight, excessive hollowing out of the groove at the grain boundary and to which is added an appearance-disappearance phenomenon of certain grain boundaries.

Thus, 1350° C. would appear to be the best compromise for obtaining an adequate image quality, i.e. which can be automatically treated or processed, without leading to a measurable evolution of the microstructure.

Batch B : The grain size density curves of FIG. 5 very clearly show that thermal etching under an oxidizing atmosphere of $CO_2$ does not lead to modifications in the distribution and average size of the grains. Etching at 1350 and 1450° C. gives an excellent result and in particular permits an automatic processing of the images.

Batch C : FIG. 6 shows an excellent superimposing of the grain size density curves, which makes it possible to affirm that thermal etching does not modify the structure of batch C. The grain boundary network is excellently revealed, e.g. at 1450° C. and permits an automatic image analysis.

EXAMPLE 6

In this example chemical etching is carried out on samples of fuels MOX 1 and MOX 2, whose characteristics have been given hereinbefore. Chemical etching was performed using two acid solutions.

There is firstly a specific chemical etching of the low plutonium enrichment areas using a solution ($H_2O$, $H_2O_2$, $H_2SO_4$), followed, after polishing, by a second chemical etching ($H_2O$, $H_2O_2$, $NH_4NF_2$) making it possible to reveal all the microstructure.

It is found that the microstructure revealed after each of the etching operations clearly illustrates the disadvantages of chemical etching, namely inter alia a different colouring of the sections of the grains and an incomplete revealing of the grain boundaries.

EXAMPLE 7

This example involves the thermal etching under a reducing atmosphere of argon with 5% hydrogen and 2600 vpm of $H_2O$ of samples of batches MOX 1 and MOX 2 at temperatures close to 1600° C. and with a plateau time of 10 to 30 minutes.

The tests lead to the revealing of the surface of the ceramic identical to that obtained on uranium oxide with in particular a resulting, non-uniform, optical image.

EXAMPLE 8

In this example, according to the invention, thermal etching takes place under an oxidizing atmosphere of samples of batches MOX 1 and MOX 2. The oxidizing atmosphere is constituted by $CO_2$ and 10 vpm of $O_2$, the etching temperature being fixed at 1350° C. and the etching time at 30 minutes.

Figure 7:
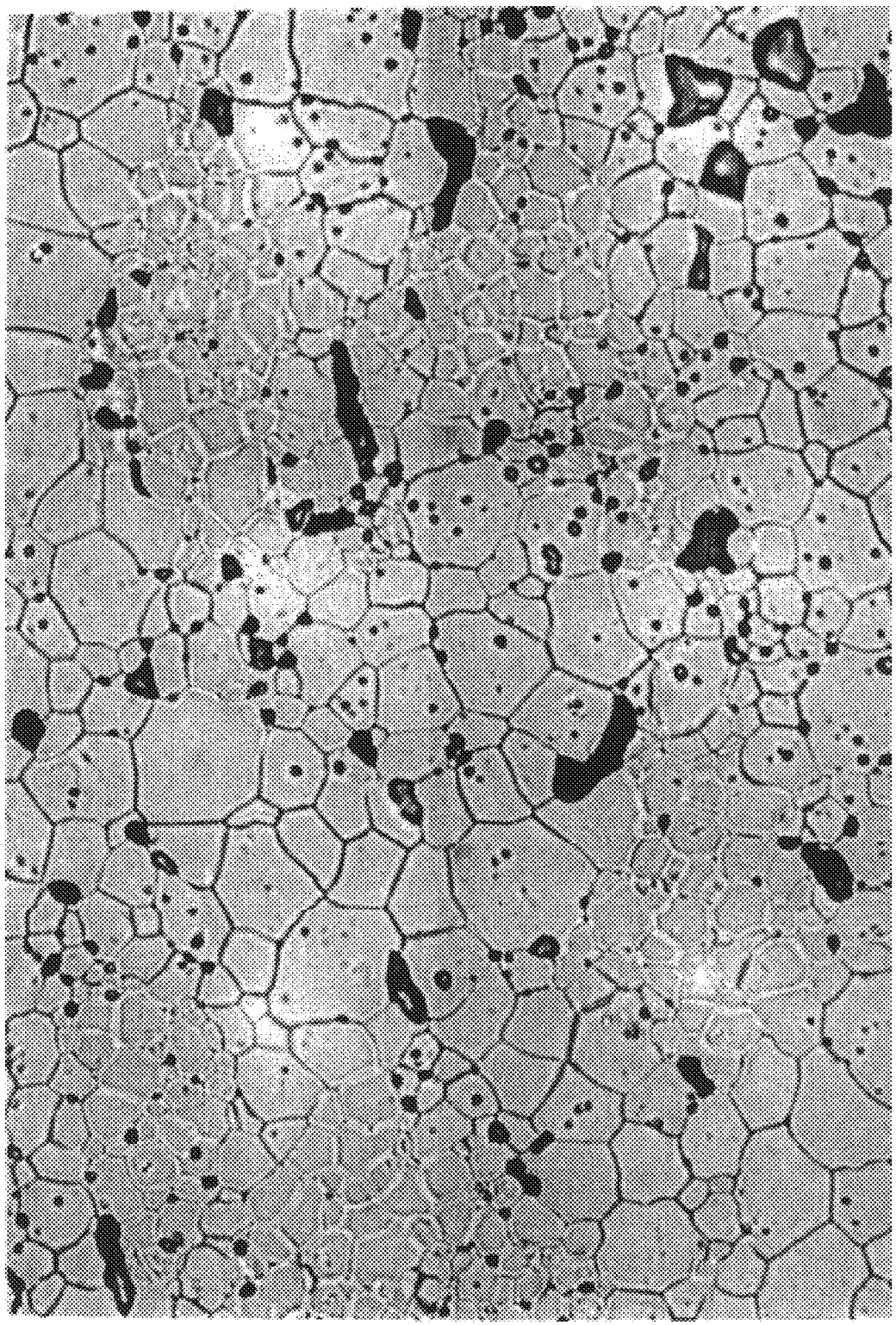
FIG. 7 is an optical image (micrograph of a sample of batch MOX 2 following thermal etching under $CO_2$+10 vpm of $O_2$ at 1350° C. and for 30 minutes.
Figure 8:
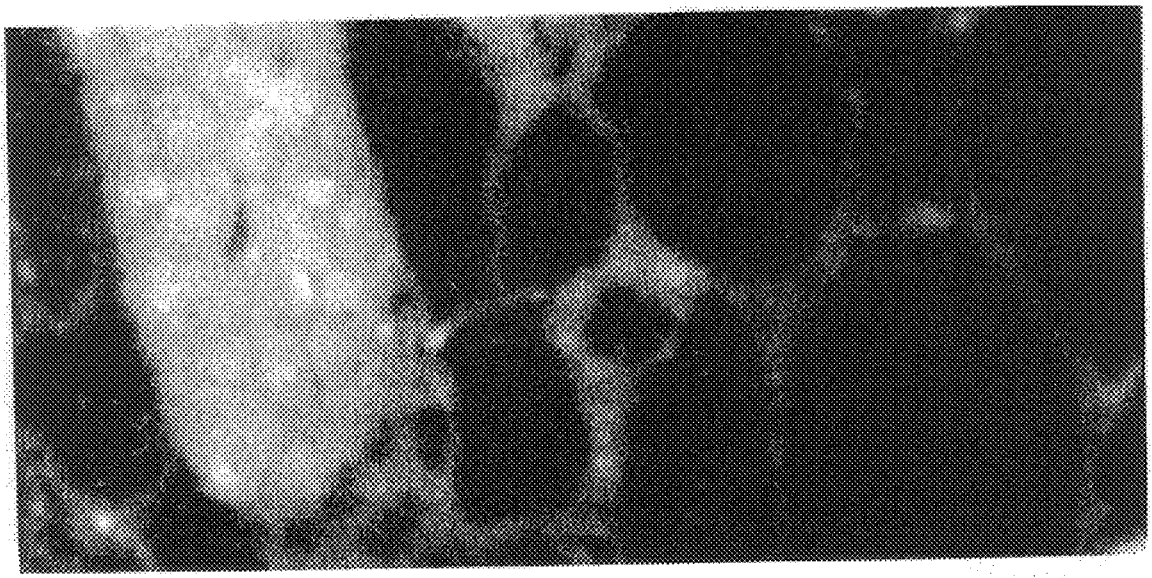
FIG. 8 is an optical image of a sample of batch MOX 1 following thermal etching under $CO_2$+10 vpm of $O_2$ at 1350° C. and for 30 minutes.

The ceramographic revealing obtained on the two samples MOX 1 and MOX 2 are shown in FIGS. 7 and 8, which are optical images of said two samples etched under $CO_2$ at 1350° C. and for 30 minutes. They show that the entire structure thereof is completely revealed.

However, the thermal etching of the grain boundaries is not uniform. The grain boundaries of certain isolated areas appear white, whereas the remainder of the grain boundaries is characterized by a black line, said configuration normally being encountered in the case of uranium dioxide grain boundaries.

Comparisons between the same areas of a ceramographic section of MOX 1 thermally etched under $CO_2$ and observed under an optical microscope and with the Castaing microprobe where then carried out.

Figure 9:
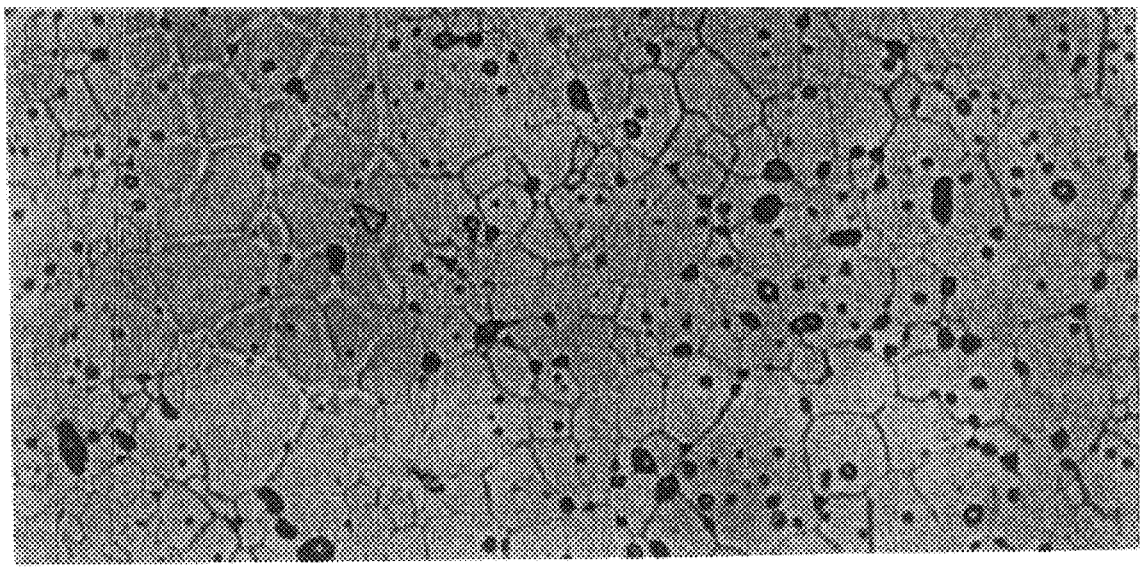
FIG. 9 is a X image corresponding to the optical image of FIG. 8.
Figure 10:
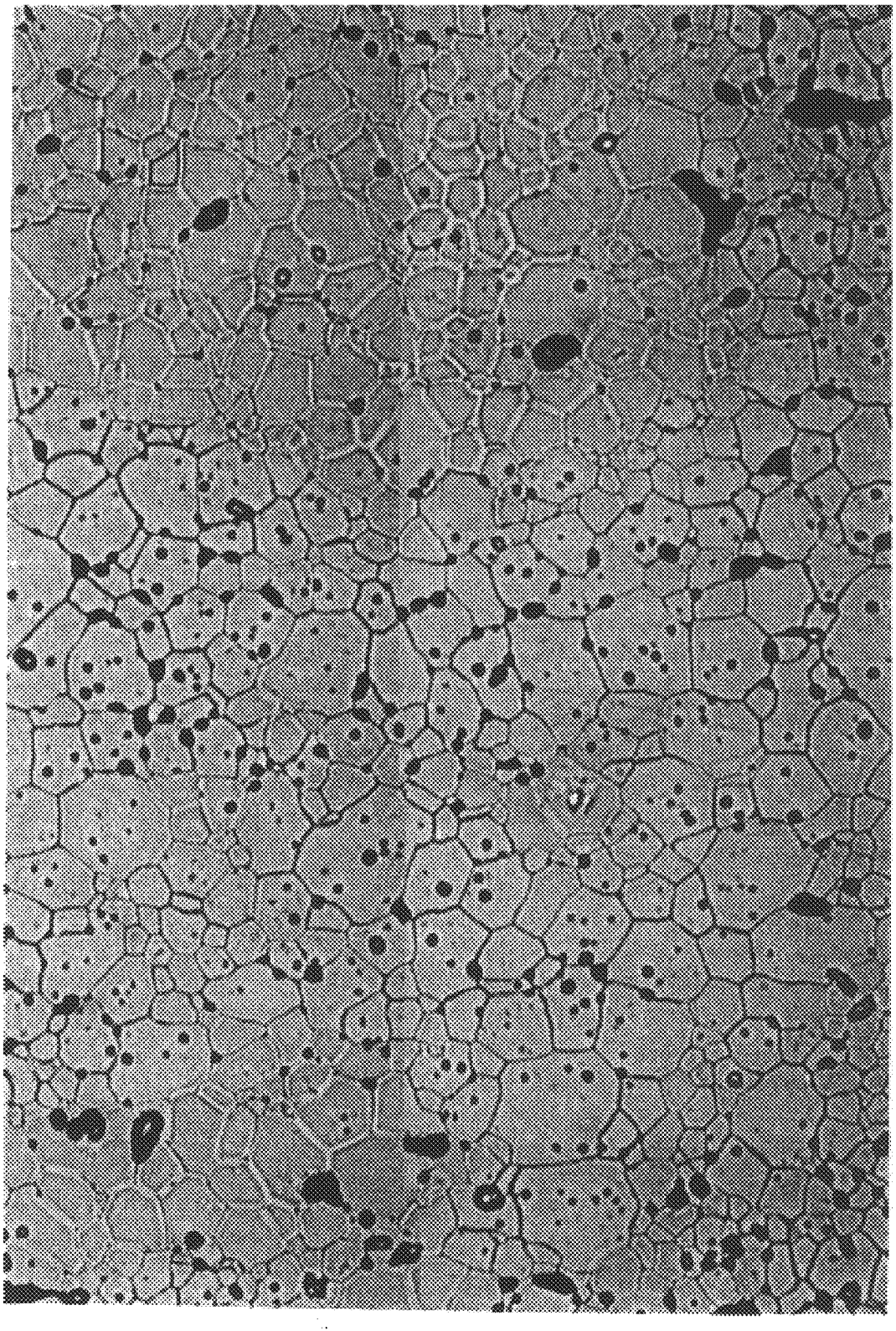
FIG. 10 is an optical image of a sample of batch MOX 1 following thermal etching under $CO_2$ and 10 vpm of $CO_2$ at 1350° C. and for 30 minutes.
Figure 11:
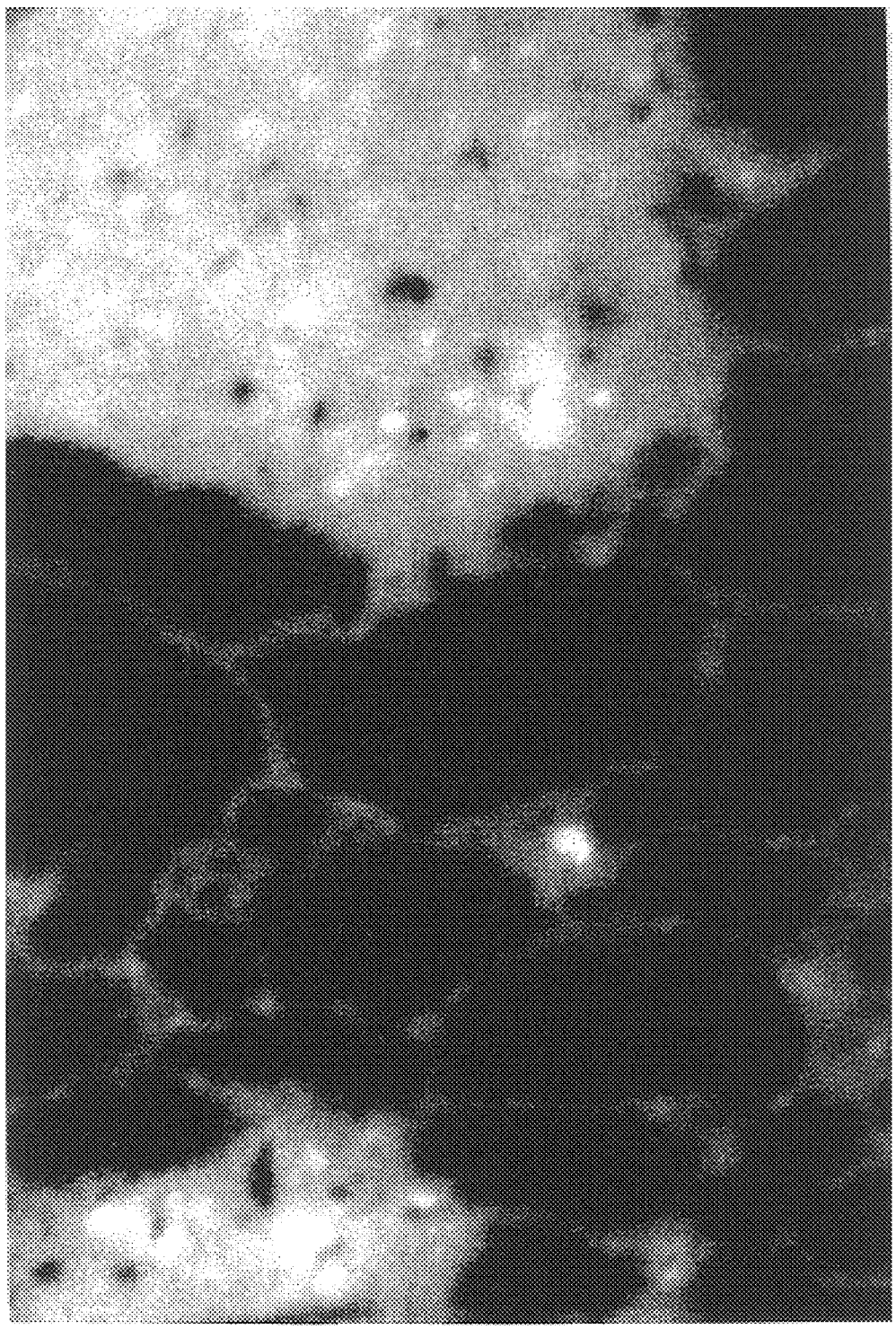
FIG. 11 is a X image corresponding to the optical image of FIG. 10.

FIGS. 8 and 10 show optical micrographs of MOX 1 obtained after thermal etching. They should be compared with FIGS. 9 and 11, which show the X images of the plutonium of said same areas obtained with the microprobe.

The higher the plutonium concentration, the clearer or brighter the characteristic area of the X image. Comparison of the optical images and the X images clearly shows that the grain boundaries appear white corresponding to plutoniferous grains (constituting islands with high plutonium contents).

Thus, there is a selective etching clearly revealing the areas with high plutonium contents (parent mixture), as compared with the areas with the lower concentrations (matrix).

It will be noted that this etching difference as a function of the local plutonium content of the grains following oxidizing thermal etching under $CO_2$ according to the invention is not reproduced during the prior art thermal etching operations performed under reducing conditions, i.e. under humidified hydrogen.

This etching difference, which constitutes one of the unexpected effected and surprising advantages of the process according to the invention when used on MOX, is probably associated with the specific oxygen chemical potential of the invention imposed by the gaseous mixture used during etching.

EXAMPLE 9

In this example, as in example 5, measurement takes place of the size of the grains and the interest is demonstrated of thermal etching under an oxidizing atmosphere of $CO_2$ under the conditions of example 8 for revealing the microstructure of MOX, making comparisons between the grain size measurements obtained by individual analysis of sections of grains following chemical etching and thermal etching.

Figure 12:
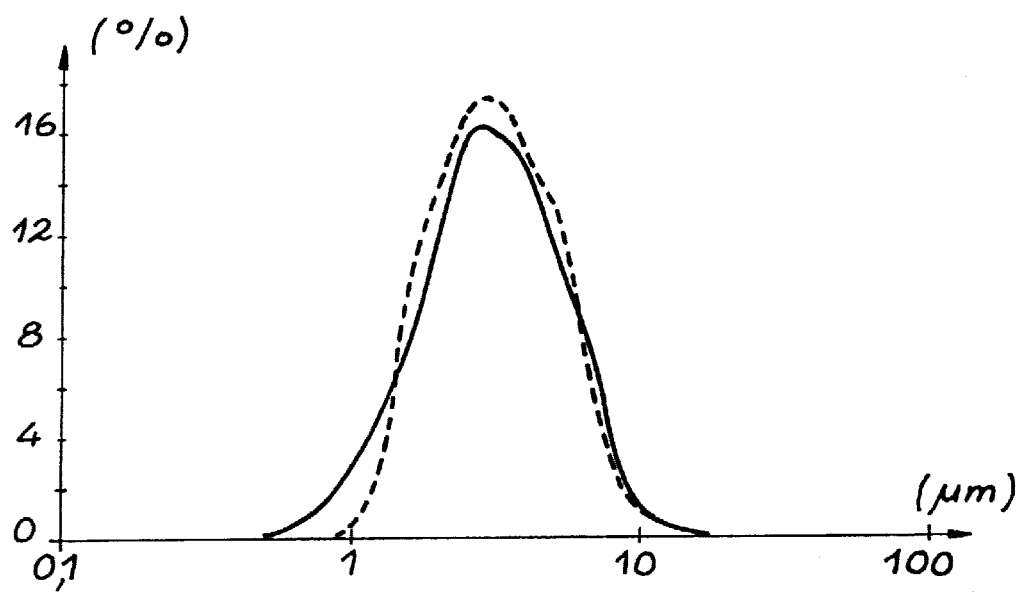
FIG. 12 is a graph identical to FIGS. 2 to 4 giving the grain size density curves of a sample of batch MOX 1 following chemical and thermal etching operations under $CO_2$+10 vpm of $O_2$ at 1350° C. and for 30 minutes.
Figure 13:
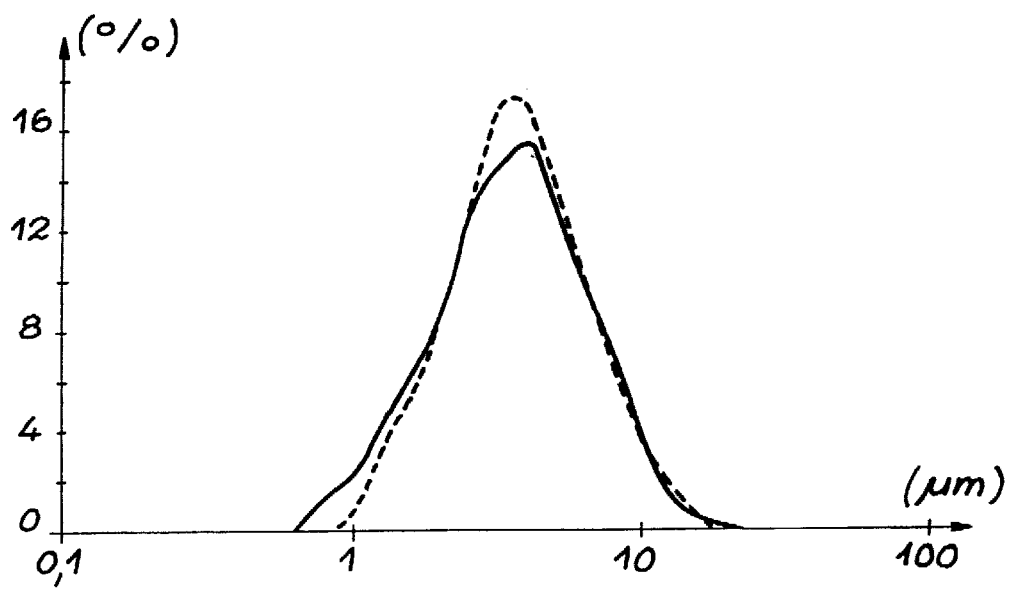
FIG. 13 is a graph identical to FIG. 12, but relating to a sample of batch MOX 2.

The grain size density curves obtained for the MOX 1 and MOX 2 samples are respectively shown in FIGS. 12 and 13, where the grain size density curves obtained after chemical etching and thermal etching (conditions of example 8) are respectively represented in dotted line and continuous line form.

The grain size density curves of the sections of grains obtained after chemical and thermal etching are comparable. Thus, oxidizing thermal etching under $CO_2$ does not modify the microstructure of MOX fuels and permits the homogeneous revealing of the grain boundaries.

EXAMPLE 10

In this example observations are made with the aid of a scanning microscope (PHILIPS FEG XL 30 field effect microscope) on one of the $UO_2$ samples (batch A) thermally etched under an oxidizing atmosphere of argon +10 vpm $O_2$ at 1650° C. and for 3 minutes, under a reducing atmosphere of hydrogen at 1650° C. and 15 minutes and under an oxidizing atmosphere of $CO_2$+10 vpm $O_2$ at 1350° C. and for 30 minutes.

Figure 14:
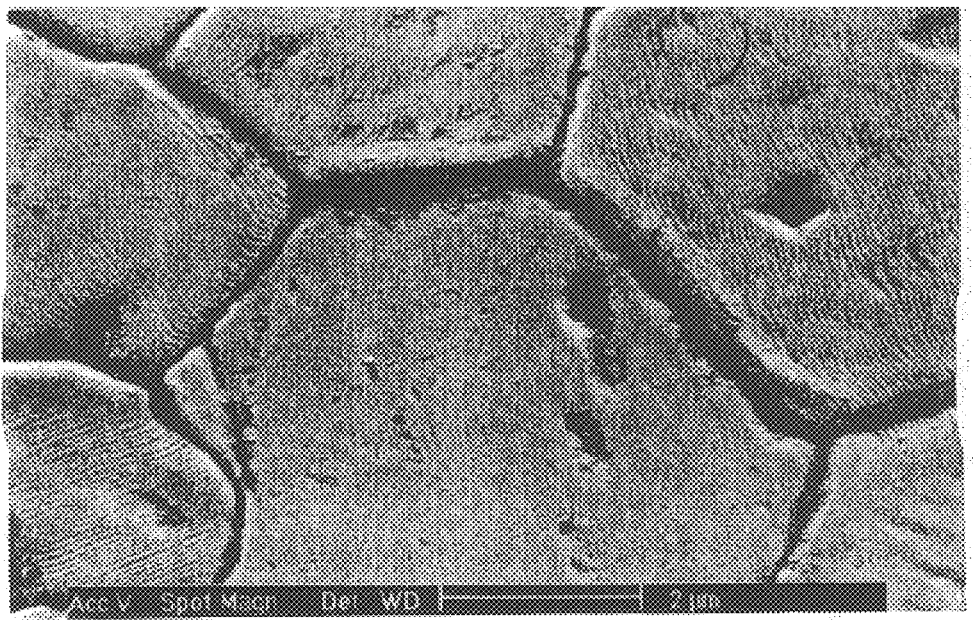
FIG. 14 is an electronic image (micrograph) of a sample of batch A ($UO_2$) etched under Ar+10 vpm $O_2$ at 1650° C., revealing an asymmetrical grain boundary.
Figure 15:
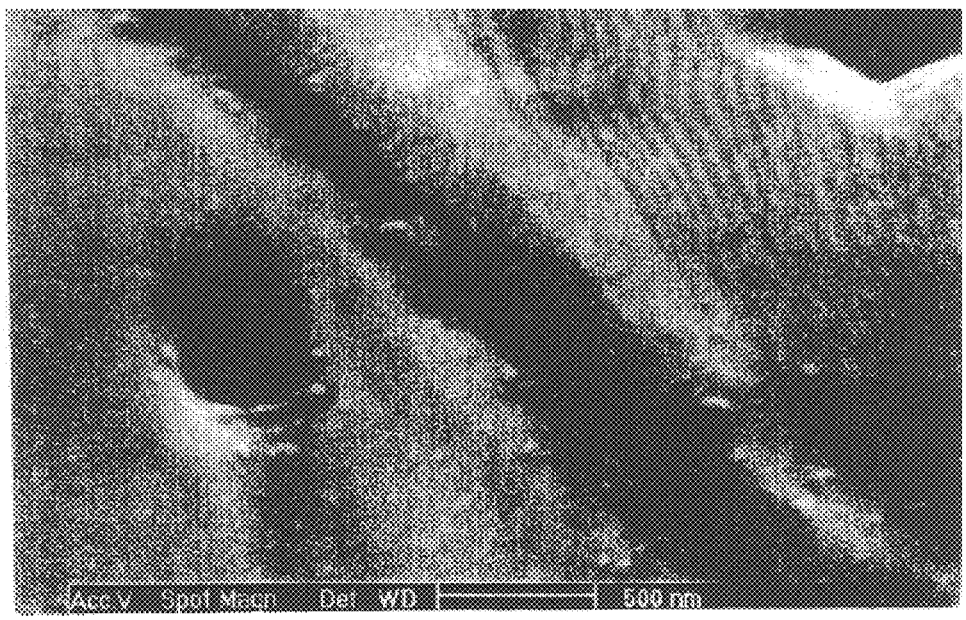
FIG. 15 is a zoom of the micrograph of FIG. 15.
Figure 16:
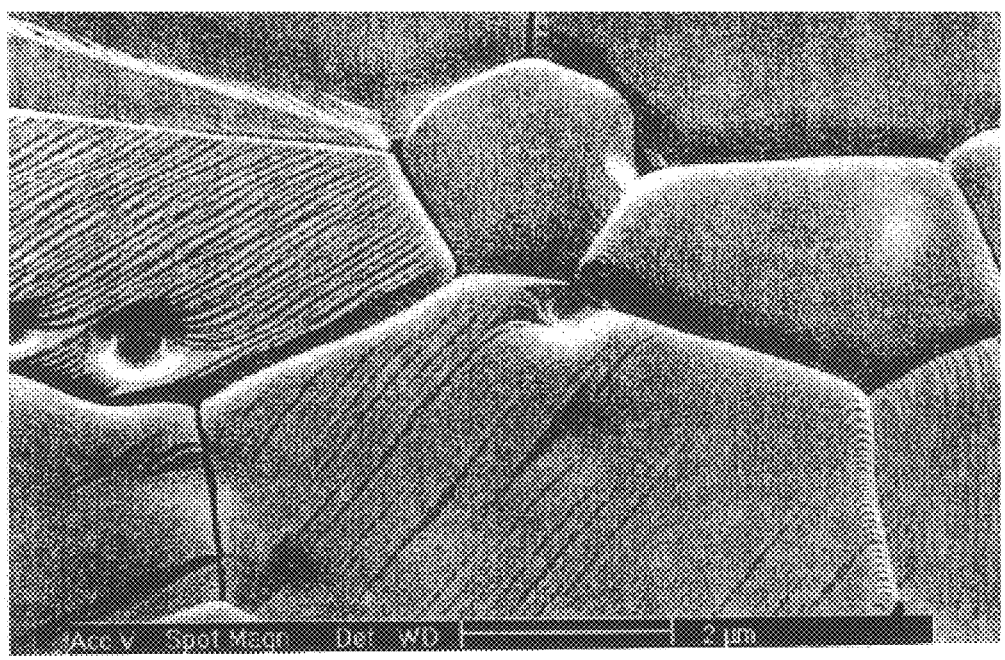
FIG. 16 is an electronic image of a sample of batch A etched under $CO_2$+10 vpm $O_2$ at 1350° C., which shows the revealing uniformity.

These observations show that under argon or $H_2$, certain grooves of grain boundaries have a clear asymmetry in their geometry (FIGS. 14 and 15). However, it should be noted that all the grain boundaries are etched and revealed, contrary to what can be observed with the optical microscope as a result of the numerical aperture of the optics used. Under $CO_2$, the surface is uniformly etched and the geometry of the grooves appears symmetrical and homogeneous (FIG. 16).

EXAMPLE 11

This example uses an atomic force microscope (A.F.M. Nanoscope 2$^{(R)}$) for precisely quantifying the geometry of the grooves at the grain boundaries for each of the oxidizing etching operations performed on $UO_2$.

Figure 17:
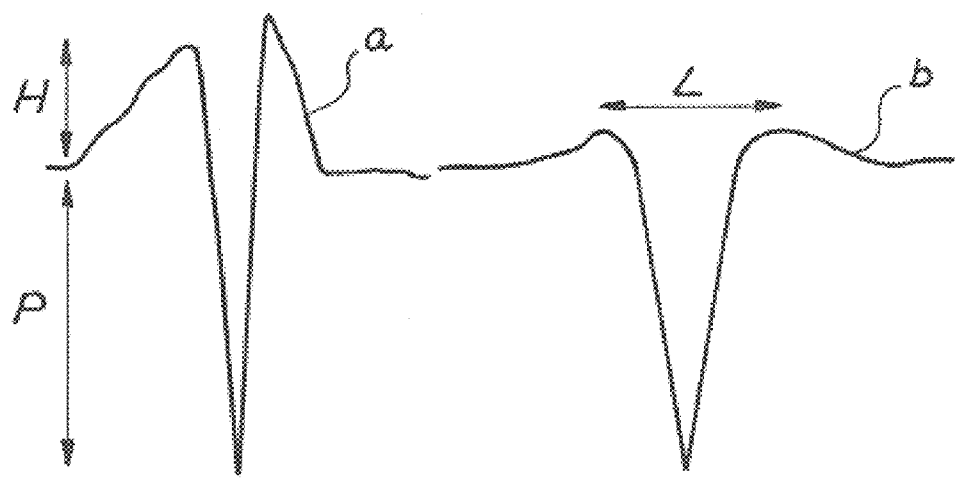
FIG. 17 is a diagram showing profiles of grain boundaries measured by the atomic force microscope (AFM) on $UO_2$ thermally etched under Ar+10 vpm of $O_2$ (profile a) and under CO+10 vpm of $O_2$ (profile b).

FIG. 17 shows two standard profiles of grain boundaries thermally revealed under Ar (profile a) and under $CO_2$ (profile b) confirming the preceding qualitative observations. The grain boundaries of the sample etched under $CO_2$ are symmetrical and have a regular geometry. The profiles measured by A.F.M. on these grain boundaries reveal no significant variation as regards depth (P), width (L) and height (H), unlike in the case of those measured on the sample etched under Ar, as is revealed by the values in table IV.

TABLE IV

Characteristic quantities of grooves at the grain boundaries measured by atomic force microscopy

| Nature of etching gas used | Min and max heights measured | Min and max widths measured* (um) | Min and max depths measured* (nm) |
| --- | --- | --- | --- |
| Argon + vpm $O_2$ | 2–10 | 0.2–1 | 7–18 |
| $CO_2$ + 10 vpm $O_2$ | 1–3 | 0.5–0.9 | 13–19 |

*Measurements performed on a total of 10 grain boundaries

The quality of the optical image of the granular structure of the sample is consequently highly conditioned by the geometry of the groove created during the thermal etching of the grain boundary.

Thus, the irregular surface of a $UO_2$ fuel revealed under Ar+10 vpm $O_2$ (or $H_2$) differently reflects the straight light beam from the optical microscope.

As a function of the groove geometry, the optical image of the microstructure will appear as non-uniform, even if all the grain boundaries are etched.

In the case of an oxidizing thermal etching under $CO_2$+10 vpm $O_2$ all the grooves are geometrically identical and the optical image of the microstructure appears uniform and can therefore be treated by an automatic image analysis algorithm.

We claim:

1. Process for thermal etching of a ceramic, in which said thermal etching is performed in a furnace under a controlled atmosphere constituted by an oxidizing gas supplying an oxygen chemical potential of −75 kJ/mole to −125 kJ/mole and comprises the following, successive stages:

rapid temperature rise of the furnace at a rate of 900° C./h to 1500° C./h from an initial temperature to a temperature plateau, maintaining the temperature of said plateau at a value of 1250° C. to 1450° C. for a period of 30 minutes to 15 minutes, lowering a temperature to the final temperature.

2. Process according to claim 1, wherein said ceramic is constituted by one or more refractory oxides of metals chosen from the group consisting of aluminium oxides, cerium oxides, metal oxides of the family of actinides such as U, Pu and Th, and mixed oxides of the family of actinides such as U, Pu and Th.

3. Process according to claim 1, wherein said ceramic is a monophase ceramic.

4. Process according to claim 2, wherein said ceramic is a polyphase ceramic.

5. Process according to claim 3, wherein said ceramic is a nuclear fuel prepared from $UO_2$ powder.

6. Process according to claim 4, wherein said ceramic is a nuclear fuel of type (U, Pu) $O_2$.

7. Process according to claim 1, wherein said oxidizing gas is constituted by a vector gas and oxygen.

8. Process according to claim 7, wherein the vector gas is chosen from the group consisting of $CO_2$, argon, other inert gases and their mixtures.

9. Process according to either of claim 7 and 8, wherein the oxidizing gas contains 10 to 3000 vpm of oxygen.

10. Process according to claim 9, wherein the oxidizing gas is constituted by $CO_2$ and 10 vpm oxygen.

11. Process according to claim 9, wherein the oxidizing gas is constituted by argon and 1000 vpm oxygen.

12. Process according to claim 1, wherein the temperature of the plateau is 1300 to 1400° C.

13. Process according to claim 12, wherein the temperature of the plateau is 1350° C.

14. Process according to claim 1, wherein the oxygen potential supplied by the oxidizing gas is approximately −100 kJ/mole.

15. Process according to claim 1, wherein the temperature drop of the furnace takes place at a rate of 900 to 1500° C./h.

16. Process according to claim 1, wherein the ceramic undergoes a polishing treatment beforehand.

17. Process for the study of the microstructure of a ceramic, wherein the granular structure of said ceramic is revealed by the thermal etching process according to claim 1 and the thus revealed structure undergoes one or more analysis, measurement or observation operations.

18. Process according to claim 17, wherein said analysis, measurement or observation operation comprises an observation of the surface of the ceramic by optical or electronic means and the measurement of the size of the grains.

19. Process according to claim 18, wherein the measurement of the size of the grains takes place by using an analysis software of images obtained associated with said optical means.

* * * * *

UNITED STATES PATENT AND TRADEMARK OFFICE
CERTIFICATE OF CORRECTION

PATENT NO.     : 6,171,511 B1
DATED          : January 9, 2001
INVENTOR(S)    : Charollais et al.

It is certified that error appears in the above-identified patent and that said Letters Patent is hereby corrected as shown below:

Column 7,
Line 55, delete "CO", and insert -- $CO_2$ --.

Column 9,
Line 2, delete "50", and insert -- 5 --.

Column 14,
Line 45, delete "the", and insert -- a --.

Column 15,
Line 1, delete "either of claim 7 and 8", and insert -- claim 7 --.

Column 16,
Line 5, delete "measurement".

Signed and Sealed this

First Day of January, 2002

Attest:

Attesting Officer

JAMES E. ROGAN
*Director of the United States Patent and Trademark Office*